United States Patent
Gassoway et al.

(10) Patent No.: US 10,123,710 B2
(45) Date of Patent: Nov. 13, 2018

(54) OPTICAL PULSE-RATE SENSOR PILLOW ASSEMBLY

(71) Applicant: MICROSOFT TECHNOLOGY LICENSING, LLC, Redmond, WA (US)

(72) Inventors: Gabriel Michael Rask Gassoway, Redmond, WA (US); Gregory Kim Justice, Redmond, WA (US); Mohammad Sakeri, Kirkland, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 242 days.

(21) Appl. No.: 14/292,447

(22) Filed: May 30, 2014

(65) Prior Publication Data

US 2015/0342529 A1    Dec. 3, 2015

(51) Int. Cl.
| | | |
|---|---|---|
| *A61B 5/02* | (2006.01) | |
| *A61B 5/024* | (2006.01) | |
| *A61B 5/00* | (2006.01) | |
| *A61B 5/0205* | (2006.01) | |
| *A61B 5/053* | (2006.01) | |

(52) U.S. Cl.
CPC ........ *A61B 5/02427* (2013.01); *A61B 5/0082* (2013.01); *A61B 5/0205* (2013.01); *A61B 5/02438* (2013.01); *A61B 5/681* (2013.01); *A61B 5/6831* (2013.01); *A61B 5/6844* (2013.01); *A61B 5/7264* (2013.01); *A61B 5/0533* (2013.01); *A61B 5/6824* (2013.01);
(Continued)

(58) Field of Classification Search
CPC ............ A61B 5/02427; A61B 5/02438; A61B 5/0261
See application file for complete search history.

(56) References Cited

U.S. PATENT DOCUMENTS

| | | |
|---|---|---|
| 4,195,642 A | 4/1980 | Price et al. |
| 8,181,881 B2 | 5/2012 | Pedicano |

(Continued)

FOREIGN PATENT DOCUMENTS

| | | |
|---|---|---|
| EP | 2888996 A1 | 7/2015 |
| WO | 2012061440 A2 | 5/2012 |

(Continued)

OTHER PUBLICATIONS

ISA European Patent Office, International Search Report and Written Opinion Issued in Application No. PCT/US2015/032768, dated Aug. 25, 2015, WIPO, 11 pages.
Fingas, Jon, "TomTom's new GPS watches track your heart rate without a chest strap (update: US pricing)", http://www.engadget.com/2014/04/03/tomtom-cardio-gps-watches/, Apr. 3, 2014, 10 pages.
Goode, Lauren, "Samsung's New Gear Fit Needs to Work on the "Fit" Part", http://recode.net/2014/04/08/samsungs-new-gear-fit-needs-to-work-on-the-fit-part/, Apr. 8, 2014, 10 pages.
(Continued)

*Primary Examiner* — Eric D. Bertram
(74) *Attorney, Agent, or Firm* — Alleman Hall Creasman & Tuttle LLP

(57) ABSTRACT

A sensory-and-logic system comprises an illumination source configured to emit a blood-sensing light, a window through which the blood-sensing light passes en route to human tissue, an illumination receiver configured to measure the blood-sensing light reflected back through the window from the human tissue, a frame surrounding the window and elevating away from the window, and a pillow surrounding the frame and recessing from the frame and the window.

10 Claims, 6 Drawing Sheets

(52) U.S. Cl.
CPC . *A61B 2560/0406* (2013.01); *A61B 2562/164* (2013.01)

(56) References Cited

U.S. PATENT DOCUMENTS

| | | | |
|---|---|---|---|
| 2006/0038188 A1* | 2/2006 | Erchak | H01L 33/20 257/82 |
| 2008/0181556 A1* | 7/2008 | Borgos | A61B 5/022 385/13 |
| 2008/0251539 A1 | 10/2008 | Yapaola et al. | |
| 2010/0145171 A1* | 6/2010 | Park | A61B 5/1455 600/324 |
| 2011/0098583 A1 | 4/2011 | Pandia et al. | |
| 2012/0316455 A1 | 12/2012 | Rahman et al. | |
| 2013/0338470 A1 | 12/2013 | Ouwerkerk | |
| 2014/0081161 A1 | 3/2014 | Kuno | |
| 2014/0142403 A1* | 5/2014 | Brumback | A61B 5/02433 600/324 |

FOREIGN PATENT DOCUMENTS

| | | | |
|---|---|---|---|
| WO | 2012125425 A2 | 9/2012 | |
| WO | 2013030744 A1 | 3/2013 | |
| WO | 2013093923 A2 | 6/2013 | |

OTHER PUBLICATIONS

"Samsung Gear Fit, Gear 2 and Gear 2 Neo go on sale worldwide", NDTV Gadgets, http://gadgets.ndtv.com/others/news/samsung-gear-fit-gear-2-and-gear-2-neo-go-on-sale-worldwide-507220, Apr. 11, 2014, 3 pages.

Poeter, Damon, "Meet Simband, Samsung's Next-Gen Health Tracker", http://www.pcmag.com/article2/0,2817,2458663,00.asp, May 28, 2014, 5 pages.

IPEA European Patent Office, Second Written Opinion Issued in Application No. PCT/US2015/032768, dated Jan. 5, 2016, WIPO, 7 pages.

Campbell, Mikey, "Review W/Me Wearable Wellness Monitor and Coach", Published on: Dec. 18, 2013, Available at: http://appleinsider.com/articles/13/12/18/review-wme-wearable-wellness-monitor-and-coach.

"Samsung Gear", Published on: Mar. 11, 2014, Available at: http://www.samsung.com/global/microsite/gear/gearfit_features.html.

"Alpha", Retrieved on: Apr. 3, 2014, Available at: http://www.mioglobal.com/docs/mio_alpha_userguide_eng.pdf.

IPEA European Patent Office, International Preliminary Report on Patentability issued in PCT Application No. PCT/US2015/032768, dated Apr. 7, 2016, WIPO, 8 pages.

* cited by examiner

OPTICAL PULSE-RATE SENSOR PILLOW ASSEMBLY

DETAILED DESCRIPTION

A wearable electronic device, such as a wrist-worn fitness tracking device, may include one or more sensors configured to measure a physical attribute of a person. For example, a wearable electronic device may include one or more electrically-conductive skin sensors, also referred to as Galvanic Skin Response (GSR) contacts, an optical pulse-rate sensor, and other types of sensors. These effectiveness of these sensors may improve if held in constant close or near contact with the skin of the user. However, given the movement of the wrist as well as differing shapes and sizes of wrists of different users, it may be difficult to maintain the sensors in close contact with the skin.

According to examples disclosed herein, an electrically-conductive skin sensor may be ring-shaped to substantially surround an optical pulse-rate sensor. The electrically-conductive skin sensor and optical pulse-rate sensor may be supported by a rigid, semi-rigid, or flexible pillow of the wearable electronic device. The electrically-conductive skin sensor and optical pulse-rate sensor may be positioned on the mound of the pillow and the pillow may urge the electrically-conductive skin sensor and optical pulse-rate sensor towards the skin of the user when the wearable electronic device is worn by the user. The pillow may include a rolling diaphragm and/or spring to independently suspend the optical pulse-rate sensor so that it maintains constant near contact with the wearer's skin, even if the user is moving vigorously. Further, the electrically-conductive skin sensor may act as a frame and include an elevated rim to seal the optical pulse-rate sensor from ambient light noise and prevent the optical pulse-rate sensor from constricting capillary flow in the vicinity of the optical pulse-rate sensor.

While described below in the context of a portable wearable electronic device, the examples of the optical pulse-rate sensor and pillow of this disclosure may be implemented with different types of sensory-and-logic systems.

Figure 1A:
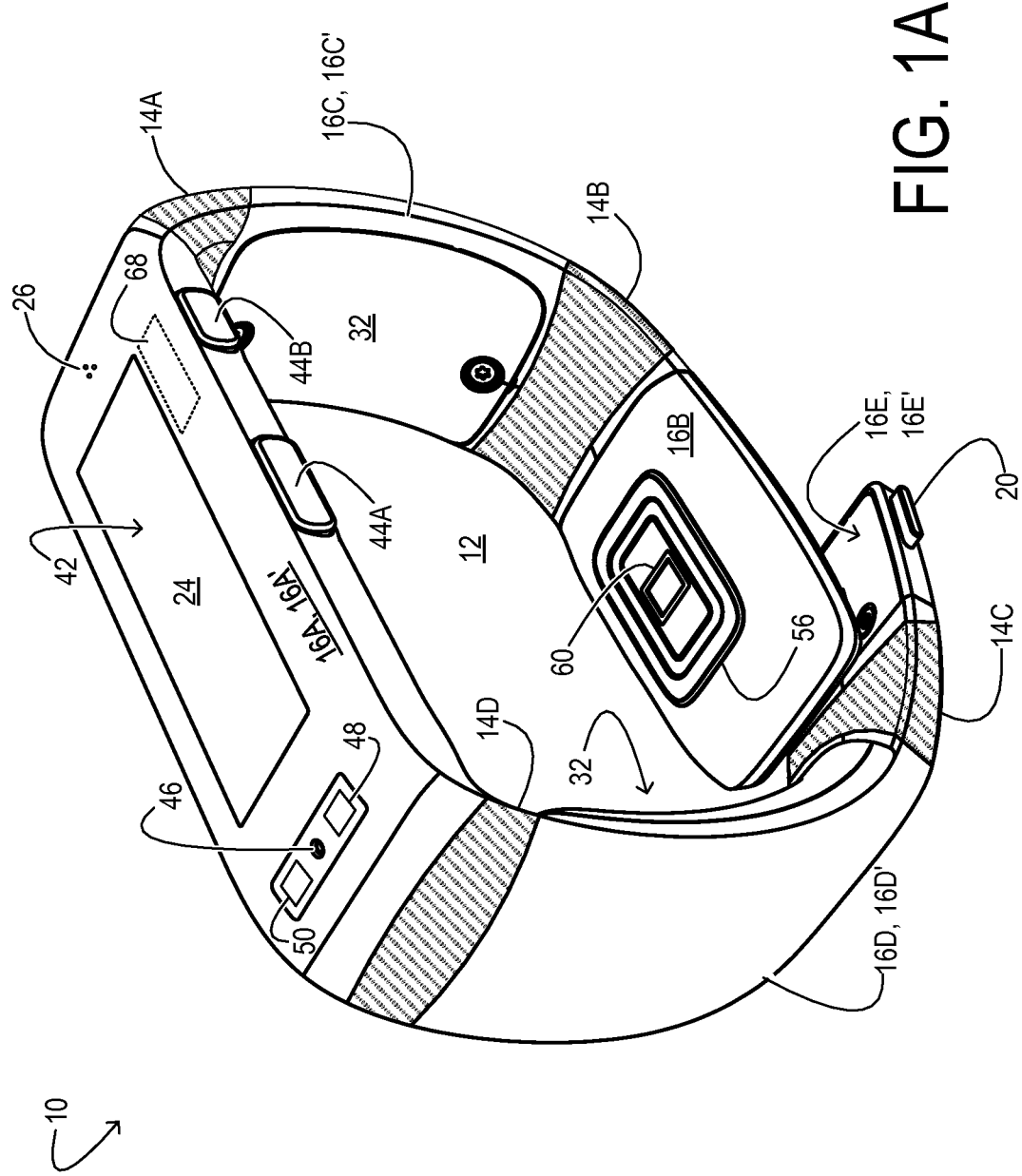
FIGS. 1A and 1B show aspects of an example wearable electronic device.
Figure 1B:
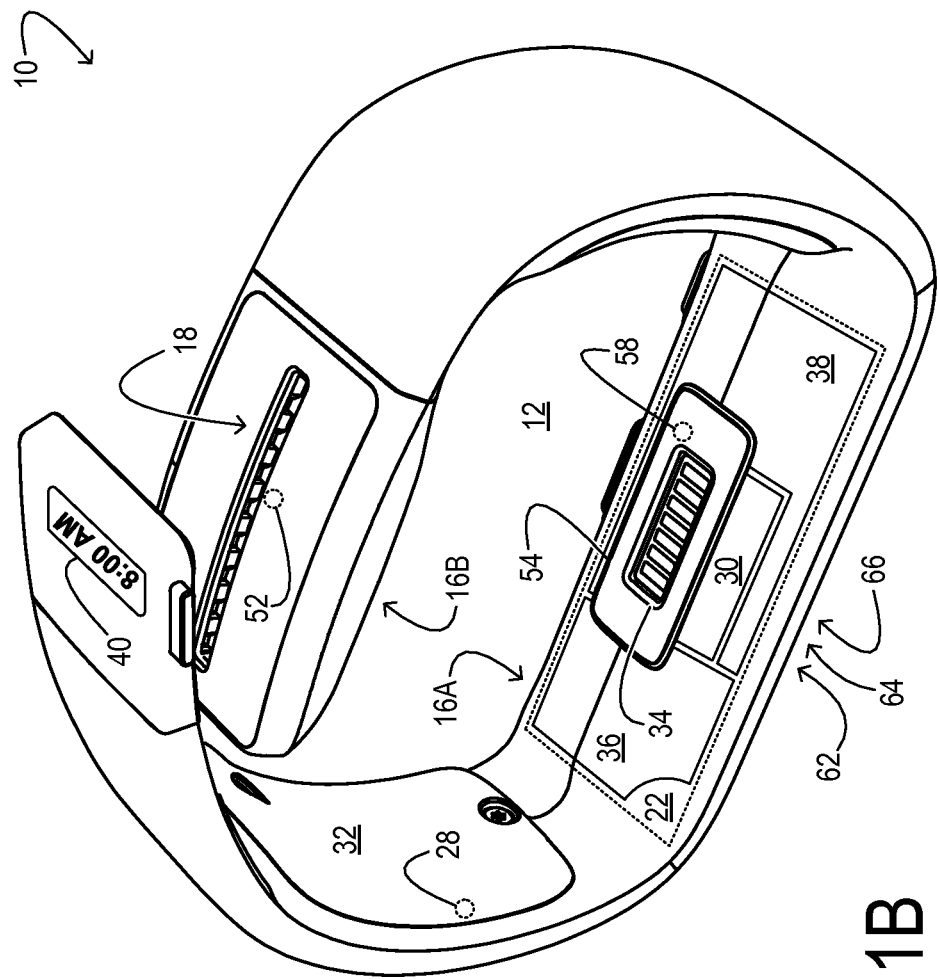

FIGS. 1A and 1B show aspects of a sensory-and-logic system in the form of a wearable electronic device 10 in one, non-limiting configuration. The illustrated device takes the form of a composite band 12, which may be worn around a wrist. Composite band 12 includes flexible segments 14A-D and rigid segments 16A-E. The terms 'flexible' and 'rigid' are to be understood in relation to each other, not necessarily in an absolute sense. Moreover, a flexible segment may be relatively flexible with respect to one bending mode and/or stretching mode, while being relatively inflexible with respect to other bending modes, and to twisting modes. A flexible segment may be elastomeric in some examples. In these and other examples, a flexible segment may include a hinge and may rely on the hinge for flexibility, at least in part.

The illustrated configuration includes four flexible segments 14A-D linking five rigid segments 16A-E. Other configurations may include more or fewer flexible segments, and more or fewer rigid segments. In some implementations, a flexible segment is coupled between pairs of adjacent rigid segments.

In one implementation, a closure mechanism (vide infra) enables facile attachment and separation of the ends of composite band 12, so that the band can be closed into a loop and worn on the wrist. In other implementations, the device may be fabricated as a continuous loop resilient enough to be pulled over the hand and still conform to the wrist. In still other implementations, wearable electronic devices of a more elongate band shape may be worn around the user's bicep, waist, chest, ankle, leg, head, or other body part. Accordingly, the wearable electronic devices here contemplated include eye glasses, a head band, an arm-band, an ankle band, a chest strap, or even an implantable device to be implanted in tissue.

As shown in FIGS. 1A and 1B, wearable electronic device 10 includes various functional components: a compute system 22, display 24, loudspeaker 26, haptic motor 28, communication suite 30, and various sensors. In the illustrated implementation, the functional components are integrated into rigid segments 16A-E—viz., display-carrier module 16A', pillow 16B', battery compartments 16C' and 16D', and buckle 16E'. This tactic protects the functional components from physical stress, from excess heat and humidity, and from exposure to water and substances found on the skin, such as sweat, lotions, salves, and the like.

In the illustrated conformation of wearable electronic device 10, one end of composite band 12 overlaps the other end. A buckle 16E' is arranged at the overlapping end of the composite band, and a receiving slot 18 is arranged at the overlapped end. As shown in greater detail herein, the receiving slot has a concealed rack feature, and the buckle includes a set of pawls to engage the rack feature. The buckle snaps into the receiving slot and slides forward or backward for proper adjustment. When the buckle is pushed into the slot at an appropriate angle, the pawls ratchet into tighter fitting set points. When release buttons 20 are squeezed simultaneously, the pawls release from the rack feature, allowing the composite band to be loosened or removed.

The functional components of wearable electronic device 10 draw power from one or more energy-storage cells 32. A battery—e.g., a lithium ion battery—is one type of energy-storage cell suitable for this purpose. Examples of alternative energy-storage cells include super- and ultra-capacitors. A typical energy storage cell is a rigid structure of a size that scales with storage capacity. To provide adequate storage capacity with minimal rigid bulk, a plurality of discrete separated energy storage cells may be used. These may be arranged in battery compartments 16C' and 16D', or in any of the rigid segments of composite band 12. Electrical connections between the energy storage cells and the functional components are routed through flexible segments 14A-D. In some implementations, the energy storage cells have a curved shape to fit comfortably around the wearer's wrist, or other body part.

In general, energy-storage cells 32 may be replaceable and/or rechargeable. In some examples, recharge power may be provided through a universal serial bus (USB) port 34, which includes a magnetic latch to releasably secure a complementary USB connector. In other examples, the energy storage cells may be recharged by wireless inductive or ambient-light charging. In still other examples, the wearable electronic device may include electro-mechanical componentry to recharge the energy storage cells from the user's adventitious or purposeful body motion. More specifically, the energy-storage cells may be charged by an electromechanical generator integrated into wearable electronic device 10. The generator may be actuated by a mechanical armature that moves when the user is moving.

In wearable electronic device 10, compute system 22 is housed in display-carrier module 16A' and situated below display 24. The compute system is operatively coupled to display 24, loudspeaker 26, communication suite 30, and to the various sensors. The compute system includes a data-storage machine 36 to hold data and instructions, and a logic machine 38 to execute the instructions.

Display 24 may be any suitable type of display, such as a thin, low-power light emitting diode (LED) array or a liquid-crystal display (LCD) array. Quantum-dot display technology may also be used. Suitable LED arrays include organic LED (OLED) or active matrix OLED arrays, among others. An LCD array may be actively backlit. However, some types of LCD arrays—e.g., a liquid crystal on silicon, LCOS array—may be front-lit via ambient light. Although the drawings show a substantially flat display surface, this aspect is by no means necessary, for curved display surfaces may also be used. In some use scenarios, wearable electronic device 10 may be worn with display 24 on the front of the wearer's wrist, like a conventional wristwatch. However, positioning the display on the back of the wrist may provide greater privacy and ease of touch input. To accommodate use scenarios in which the device is worn with the display on the back of the wrist, an auxiliary display module 40 may be included on the rigid segment opposite display-carrier module 16A'. The auxiliary display module may show the time of day, for example.

Communication suite 30 may include any appropriate wired or wireless communications componentry. In FIGS. 1A and 1B, the communications suite includes USB port 34, which may be used for exchanging data between wearable electronic device 10 and other computer systems, as well as providing recharge power. The communication suite may further include two-way Bluetooth, Wi-Fi, cellular, near-field communication, and/or other radios. In some implementations, the communication suite may include an additional transceiver for optical, line-of-sight (e.g., infrared) communication.

In wearable electronic device 10, touch-screen sensor 42 is coupled to display 24 and configured to receive touch input from the user. Accordingly, the display may be a touch-sensor display in some implementations. In general, the touch sensor may be resistive, capacitive, or optically based. Push-button sensors (e.g., microswitches) may be used to detect the state of push buttons 44A and 44B, which may include rockers. Input from the push-button sensors may be used to enact a home-key or on-off feature, control audio volume, microphone, etc.

FIGS. 1A and 1B show various other sensors of wearable electronic device 10. Such sensors include microphone 46, visible-light sensor 48, ultraviolet sensor 50, and ambient-temperature sensor 52. The microphone provides input to compute system 22 that may be used to measure the ambient sound level or receive voice commands from the user. Input from the visible-light sensor, ultraviolet sensor, and ambient-temperature sensor may be used to assess aspects of the user's environment. In particular, the visible-light sensor can be used to sense the overall lighting level, while the ultraviolet sensor senses whether the device is situated indoors or outdoors. In some scenarios, output from the visible light sensor may be used to automatically adjust the brightness level of display 24, or to improve the accuracy of the ultraviolet sensor. In the illustrated configuration, the ambient-temperature sensor takes the form a thermistor, which is arranged behind a metallic enclosure of pillow assembly 16B', next to receiving slot 18. This location provides a direct conductive path to the ambient air, while protecting the sensor from moisture and other environmental effects.

FIGS. 1A and 1B show a pair of electrically-conductive skin contact sensors—charging contact sensor 54 arranged on display-carrier module 16A', and pillow contact sensor 56 arranged on pillow assembly 16B'. Charging contact sensor 54 and pillow contact sensor 56 may be electrically-conductive skin sensors sized and shaped to form an electrical connection with human skin.

Each contact sensor contacts the wearer's skin when wearable electronic device 10 is worn. The contact sensors may include independent or cooperating sensor elements, to provide a plurality of sensory functions. For example, the contact sensors may provide an electrical resistance and/or capacitance sensory function responsive to the electrical resistance and/or capacitance of the wearer's skin. To this end, the two contact sensors may be configured as a galvanic skin-response sensor, for example. Compute system 22 may use the sensory input from the contact sensors to assess whether, or how tightly, the device is being worn, for example. In the illustrated configuration, the separation between the two contact sensors provides a relatively long electrical path length, for more accurate measurement of skin resistance.

In some examples, a contact sensor may also provide measurement of the wearer's skin temperature. In the illustrated configuration, a skin temperature sensor 58 in the form a thermistor is integrated into charging contact sensor 54, which provides direct thermal conductive path to the skin. Output from ambient-temperature sensor 52 and skin temperature sensor 58 may be applied differentially to estimate of the heat flux from the wearer's body. This metric can be used to improve the accuracy of pedometer-based calorie counting, for example. In addition to the contact-based skin sensors described above, various types of non-contact skin sensors may also be included.

Arranged inside pillow contact sensor 56 in the illustrated configuration is an optical pulse-rate sensor 60. The optical pulse-rate sensor may include a narrow-band (e.g., green) LED emitter and matched photodiode to detect pulsating blood flow through the capillaries of the skin, and thereby provide a measurement of the wearer's pulse rate. In the illustrated configuration, optical pulse-rate sensor 60 and display 24 are arranged on opposite sides of the device as worn. The pulse-rate sensor could alternatively be positioned directly behind the display for ease of engineering. In some implementations, however, a better reading is obtained when the sensor is separated from the display.

Wearable electronic device 10 may also include motion sensing componentry, such as an accelerometer 62, gyroscope 64, and magnetometer 66. The accelerometer and gyroscope may furnish inertial data along three orthogonal axes as well as rotational data about the three axes, for a combined six degrees of freedom. This sensory data can be used to provide a pedometer/calorie-counting function, for example. Data from the accelerometer and gyroscope may be combined with geomagnetic data from the magnetometer to further define the inertial and rotational data in terms of geographic orientation.

Wearable electronic device 10 may also include a global positioning system (GPS) receiver 68 for determining the wearer's geographic location and/or velocity. In some configurations, the antenna of the GPS receiver may be relatively flexible and extend into flexible segment 14A. In the configuration of FIGS. 1A and 1B, the GPS receiver is far removed from optical pulse-rate sensor 60 to reduce interference from the optical pulse-rate sensor. More generally, various functional components of the wearable electronic device—display 24, compute system 22, GPS receiver 68, USB port 34, microphone 46, visible-light sensor 48, ultraviolet sensor 50, and skin temperature sensor 58—may be located in the same rigid segment for ease of engineering, but the optical pulse-rate sensor may be located elsewhere to reduce interference on the other functional components.

As described hereinabove, the various functional components, sensors, energy-storage cells, etc., of wearable electronic device 10 are distributed among multiple rigid segments. Accordingly, one or more of the intervening flexible segments may include a course of electrical conductors running between adjacent rigid segments, inside or through the intervening flexible segment. The course of electrical conductors may include conductors that distribute power, receive or transmit a communication signal, or carry a control or sensory signal from one functional component of the device to another. In some implementations, a course of electrical conductors may be provided in the form of a flexible printed-circuit assembly (FPCA), which also may physically support various electronic and/or logic components (vide infra).

Figure 2:
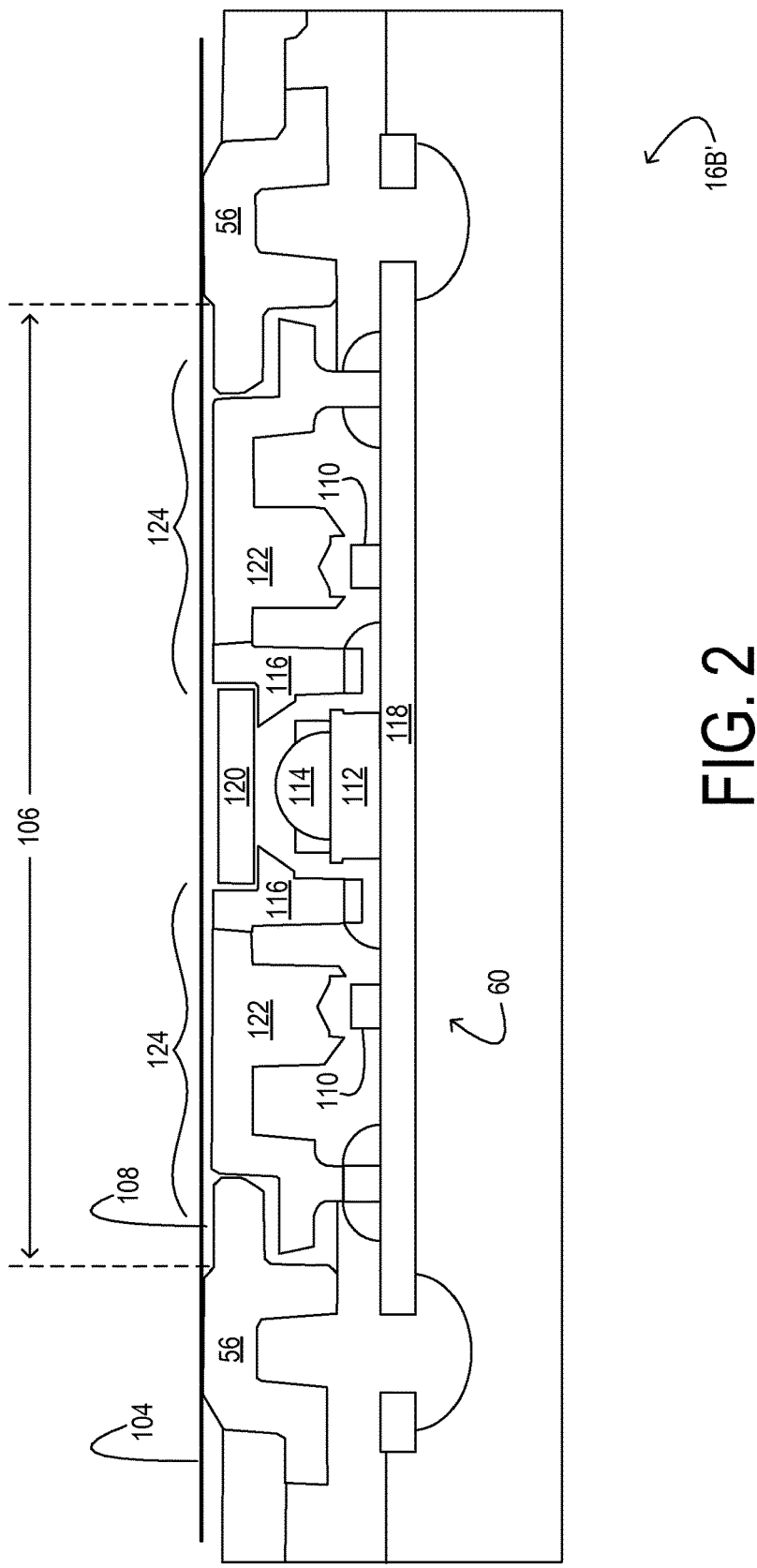
FIGS. 2 and 3 are cross-sectional views of an example optical pulse-rate sensor in a wearable electronic device including a first example of a pillow assembly.
Figure 3:
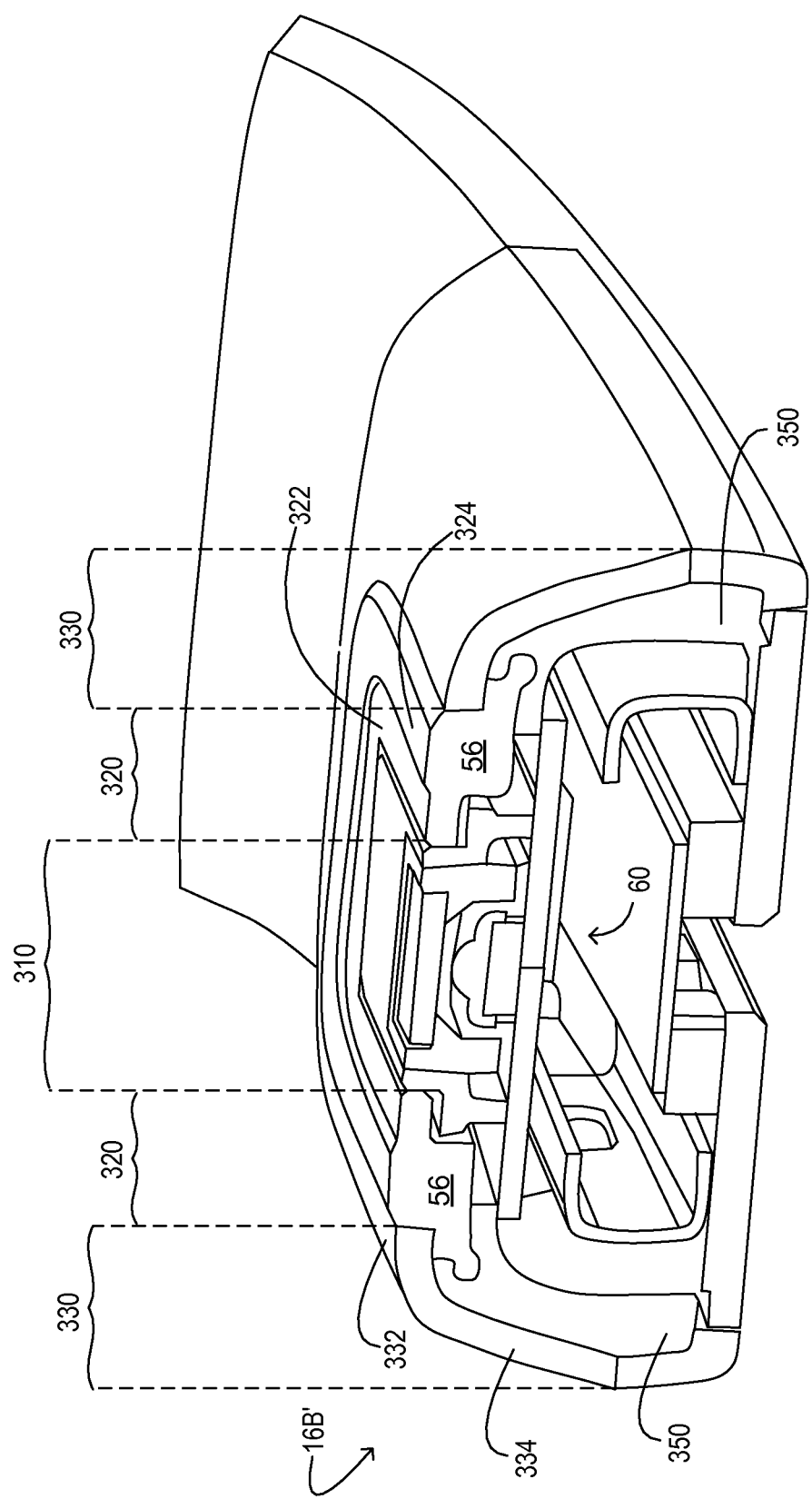

FIG. 2 provides a first cross-sectional view of pillow assembly 16B' and optical pulse-rate sensor 60, and FIG. 3 provides a second cross-sectional view of pillow assembly 16B' and optical pulse-rate sensor 60. As shown in FIG. 2, pillow contact sensor 56 is configured to contact a skin surface 104 of the wearer of wearable electronic device 10, and to enclose an area 106 of that surface. This is the area of skin through which the wearer's pulse rate is to be measured. As described hereinabove, optical pulse-rate sensor 60 may be integrated into a composite band 12 (of FIGS. 1A and 1B), which is connected to the pillow and configured to press the pillow contact sensor against the skin surface when the wearable electronic device is worn.

In the implementation illustrated in FIGS. 2 and 3, optical pulse-rate sensor 60 includes a recess portion 108 inside a frame (embodied herein as the pillow contact sensor 56), which reduces contact pressure on area 106 when the frame is in contact with skin surface 104. This feature may help to avoid a 'bleaching' effect, where excessive contact pressure hinders the refill of blood into the capillaries directly above area 106, causing a reduction in signal. Thus, the recess portion serves both to improve signal recovery times by allowing blood to re-enter bleached skin more quickly, and to prevent bleaching-based signal loss. In this manner, the recess portion can make the sensor more accurate, especially when the user is exercising vigorously, such that movement of the device on the skin is likely to occur. In some configurations and use scenarios, recess portion 108 is low enough to escape contact with skin surface 104, thereby preventing any reduction in signal due to bleaching. In other configurations, the recess portion may be higher, so that the skin surface is contacted in area 106, but with less pressure.

In still other configurations, the recess portion may be omitted entirely, so that the optical pulse-rate sensor profile is substantially flat.

The frame and recess portion 108, if included, may be formed in any suitable manner. In the illustrated configuration, pillow contact sensor 56 (the frame) has a slight step in its outer surface (the surface that contacts the wearer's skin), described in more detail below with respect to FIG. 3. As such, the outer portion of the pillow contact sensor is higher than the inner portion of the pillow contact sensor, and higher than the recessed componentry of optical pulse-rate sensor 60 which the pillow contact sensor circumscribes.

In the illustrated example, optical pulse-rate sensor 60 includes a pair of light emitters 110 coupled to pillow assembly 16W and positioned opposite area 106. As explained in more detail below, each light emitter may be configured to emit a blood-sensing light in order to measure the pulse-rate of the wearer. A light sensor 112 is also coupled to this fixture and positioned opposite the area 106. In the illustrated configuration, a hemispherical lens 114 is positioned over the light sensor to increase the amount of light from area 106 that is received into the acceptance cone of the light sensor. By placing this lens directly on the light sensor—the lens having a diameter that closely matches the width and height of the light sensor—improved collection efficiency is achieved. In particular, the effective area of the light sensor is increased by a factor equal to the magnification of the lens. In some examples, the lens is formed as a separate molded part or as a precise droplet of UV cureable optical adhesive. In other examples, the lens may be molded into the clear plastic package of the light sensor.

In the configuration of FIG. 2, optical pulse-rate sensor 60 also includes light stop 116. The light stop is coupled to pillow assembly 16B' and positioned between light emitters 110 and light sensor 112. The purpose of the light stop is to shield the light sensor and lens from direct illumination by the light source, for increased signal-to-noise.

To reduce power consumption in optical pulse-rate sensor 60, each light emitter 110 may be a high-efficiency, narrow-band light emitting diode (LED). In particular, green LEDs may be used, whose emission closely matches the absorption maximum of hemoglobin. Various numbers and arrangements of light emitters may be used without departing from the scope of this disclosure. The illustrated example shows two light emitters arranged symmetrically on opposite sides of light sensor 112.

In one implementation, light sensor 112 may be a photodiode. In other implementations, a phototransistor or other type of light sensor may be used. In the configuration shown in FIG. 2, light emitters 110 and light sensor 112 are coupled to pillow PCA 118. The pillow PCA may also include electronics configured to drive the light emitter, receive output from the light sensor, and based on the output, to generate data responsive to a pulse rate of blood flowing under the skin surface. In other implementations, at least some of the electronics may be situated elsewhere—in display-carrier module 16A', for example—or distributed between the pillow PCA and any other fixture on the device.

In the configuration of FIG. 2, an optical filter 120 is positioned over light sensor 112 and lens 114 to limit the wavelength range of light received into the light sensor. In the illustrated configuration, light stop 116 is shaped to seat the optical filter. The optical filter may be configured to transmit light in the emission band of light emitters 110, but to block light of other wavelengths, such as broadband ambient light that may leak under the rim of the pillow contact sensor. In some implementations, the optical filter is a bandpass filter with a pass band matched to the emission band of the light emitters. The optical filter may be a dichroic filter in one implementation. The use of a dichroic filter offers a manufacturing advantage over an absorbing filter. In particular, a dichroic filter can be attached using an ultraviolet (UV) curable glue. UV light can pass through the dichroic filter where the glue is applied and not be attenuated. By using a dichroic filter, a very narrow bandpass can be achieved, while simultaneously curing with light of a wavelength range outside the pass band of the filter. As the function of the dichroic is dependent on an air gap, it is possible to cure with light outside the passband, in contrast to an absorbing filter. In another implementation, the optical filter may be another type of non-absorbing interference filter, or a holographic filter which discriminates according to angle of the light received in addition to wavelength.

The illustrated optical pulse-rate sensor 60 also includes a light guide 122. The light guide is configured to collect the angle-distributed emission from light emitters 110 and redirect the emission towards skin surface 104. The light guide is further configured to disperse the emission to substantially cover area 106.

Light guide 122 may be fabricated from any suitable transparent polymer, such as polyacrylic. The light guide may be surrounded by air or by a cladding of a lower refractive index than the polymer from which the light guide is fabricated. Accordingly, the light guide may be configured to redirect and disperse collected emission via total internal reflection. Through repeated internal reflections at the boundary surfaces of the light guide, the propagating light changes direction and diverges to all regions of area 106. In particular, the boundary edges of the light guide direct the light to spread out into regions of area 106 from which the unabsorbed portion will reflect directly into light sensor 112. This feature increases the signal-to-noise ratio of the optical pulse-rate measurement.

In one implementation, light stop 116 and light guide 122 may be formed in the same mold, to create a housing 124 that attaches to the PCA over the light emitters, lens, and light sensor. In one configuration, the housing includes two different plastics. The first plastic is an optically opaque black plastic that surrounds the light sensor on four sides to form light stop 116. The rest of the housing may be made of a clear plastic, thus forming light guide 122. In one example, the composite housing is attached to pillow assembly 16B' with an optically opaque black glue. In another example, an optically clear glue may be used, or a die-cut adhesive. In these and other examples, an optically opaque black glue may be applied between light stop 116 and pillow PCA 118, for added light-blocking.

In one implementation, optical pulse-rate sensor 60 is sealed around its periphery and securely attached to pillow assembly 16B'. In one implementation, housing 124 is datumed through a hole in the pillow, and this joint is sealed with adhesive.

As noted above, pillow assembly 16W is a fixture for various internal sensory components, including optical pulse-rate sensor 60. Additionally, pillow assembly 16W provides structure for elevating optical pulse-rate sensor 60 above the band of wearable electronic device 10 while providing at least some compression to prevent movement of optical pulse-rate sensor 60 relative to the skin of the wearer. Further, to prevent capillary compression, it is desired to keep optical pulse-rate sensor 60 from compressing the skin of the wearer of the wearable electronic device 10.

Pillow contact sensor 56, which surrounds optical pulse-rate sensor 60, includes a rim elevated above optical pulse-rate sensor 60 to seal optical pulse-rate sensor 60 from outside ambient light and limiting a force with which the optical pulse-rate sensor 60 contacts the skin of the wearer. When wearable electronic device 10 is worn by a user, the rim of the pillow contact sensor is substantially sealed against the user's skin, which prevents ambient light from reaching the internal components of the optical pulse-rate sensor. In this manner, a potential noise source for the pulse measurement is greatly reduced. It will be noted that the ambient light-blocking rim structure of pillow contact sensor 56 is independent of the sensory function of this component (vide supra). Other implementations may include a frame having no sensory function per se (e.g., pillow contact sensor 56 may be omitted and another non-sensory function frame structure including a rim may instead be included).

Thus, optical pulse-rate sensor 60 includes an illumination source configured to emit a blood-sensing light (light emitter 110), a window through which the blood-sensor light passes en route to a target such as human tissue (e.g., light guide 122), and an illumination receiver (light sensor 112) configured to measure the blood-sensing light reflected back through the window (i.e., optical filter 120) from the human tissue. As illustrated in FIG. 3, the window 310 of the optical pulse rate sensor 60 includes one or more components of the optical-pulse rate sensor configured to face the skin of the user of the wearable electronic device (e.g., positioned optically intermediate the illumination receiver and/or illumination source and the human skin). The window 310 may include one or more of the housing 124, optical filter 120, light stop 116, and light guide 122, for example.

As also shown in FIG. 3, a frame 320 encircles optical pulse-rate sensor 60 and elevates away from window 310. Frame 320 includes an inner frame portion 322 surrounding window 310. In the illustrated example, pillow contact sensor 56 acts as frame 320. The inner frame portion 322 and window 310 may be substantially level (e.g., have the same vertical height) in one example. In other examples, window 310 may be recessed from inner frame portion 322. Frame 320 includes an outer frame portion 324 surrounding inner frame portion 322 that is elevated above inner frame portion 322 and window 310, also referred to herein as a rim. Outer frame portion 324 may be continuous with inner frame portion 322 (e.g., formed as one piece and/or in face-sharing contact). In one example, outer frame portion 324 may be elevated above inner frame portion 322 by a suitable amount, such as in a range of 0.1-0.2 mm. Such a relatively small amount of height difference between the inner and outer frame portions may prevent bleaching due to compression of capillaries in the area around the optical pulse-rate sensor 60 while still allowing a sufficient amount of blood-sensing light to be reflected from the wearer's skin in order to accurately measure the wearer's pulse rate.

Pillow assembly 16B' also includes a pillow 330 surrounding the frame 320 and recessing from the frame 320 and the window 310. Pillow 330 includes a first region 332 surrounding the frame 320 and a second region 334 continuous with the first region 332. First region 332 may be substantially flat, extending out from frame 320 by a suitable amount, such as 1 mm. The second region 334 slopes downward to a terminal end of the pillow 330. The second region 334 may have a suitable slope, such as sloping downward at a 45 degree angle. A difference in vertical height from a terminal end of the pillow to where the first region of the pillow meets the frame may be in a range of 2-5 mm. Additionally, frame 320 and window 310 may be elevated above the first region 332 of the pillow 330 by a suitable amount, such as in a range of 0.4-0.6 mm.

Pillow 330 may be comprised of a suitable material. In one example, pillow 330 may be relatively rigid, for example pillow 330 may comprise a thin piece of material overmolded on a rigid housing 350. The material comprising pillow 330 may be a thermoplastic having a low compressibility, such as 60 durometers. The pillow material may provide a suitable amount of friction with the skin of the wearer to maintain a tight seal with the skin. In other examples, pillow 330 may be relatively flexible and/or include a spring element, as described in more detail below with respect to FIGS. 4A, 4B, and 5.

As explained previously, optical pulse-rate sensor 60 and frame 320 may be incorporated as part of a wrist band assembly (e.g., band 12 of FIGS. 1A and 1B) configured to encircle a wrist of a user when the wrist band assembly is worn by the user. The wrist band assembly may include a latching mechanism (buckle 16E' of FIG. 1A) positioned under the optical pulse-rate sensor, frame, and pillow. The latching mechanism may urge the pillow, frame, and optical pulse-rate sensor upward such that only the frame is in contact with the wrist of the user when the latching mechanism is latched.

Figure 4A:
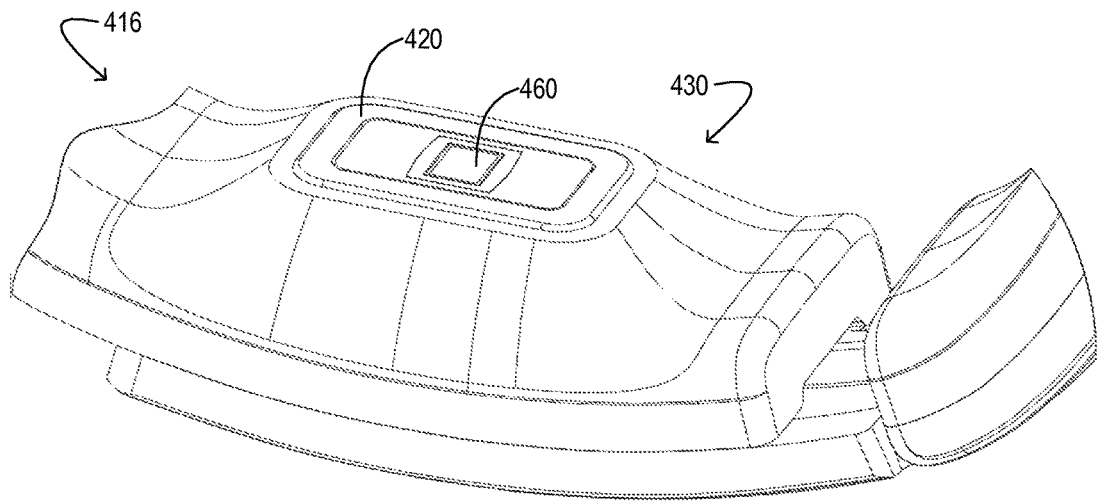
FIGS. 4A and 4B show aspects of a second example of a pillow assembly.
Figure 4B:
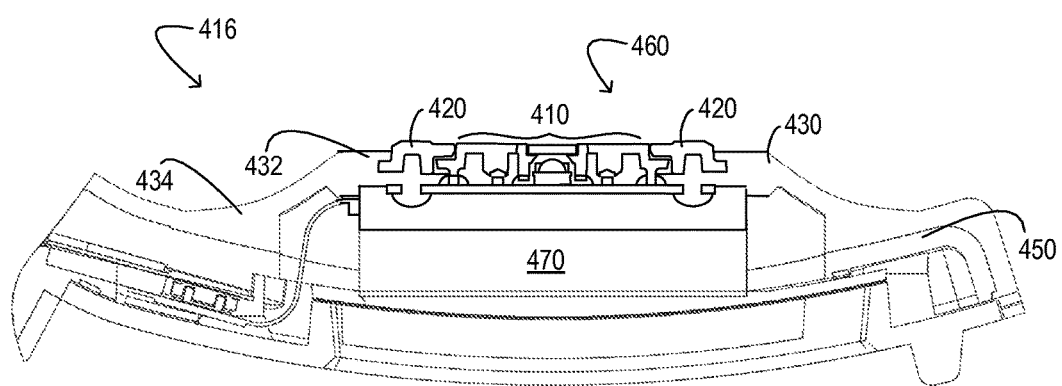

Turning now to FIGS. 4A and 4B, another example of a pillow assembly is illustrated. FIG. 4A illustrates a perspective view and FIG. 4B illustrates a cross-sectional view of a pillow assembly 416. Pillow assembly 416 may include substantially similar elements as pillow assembly 16B', including an optical pulse-rate sensor 460 (which include similar elements as optical pulse-rate sensor 60, including a window 410), frame 420 (which may be an electrically-conductive skin sensor such as a galvanic response sensor in one example), PCA, etc.

While pillow assembly 416 includes a pillow 430, it may be thicker and more flexible than pillow 330 of pillow assembly 16B'. For example, pillow 430 may be thicker (e.g., having a vertical height of 5 mm or more) and configured to be compressible by 2 mm or more. Further, in some examples, a spring element 470 may be positioned under optical pulse-rate sensor 460 to bias the optical pulse-rate sensor 460 and frame 420 towards the skin of a wearer. Pillow 430 includes a first region 432 surrounding frame 420 and second region 434 continuous with first region 432. First region 432 may be flat and extend out from frame 420. Second region 434 may recess away from first region 432, e.g., second region 434 may slope downward toward a terminal end of the pillow 430. Pillow 430 may be comprised of a soft thermoplastic material overmolded on housing 450.

Figure 5:
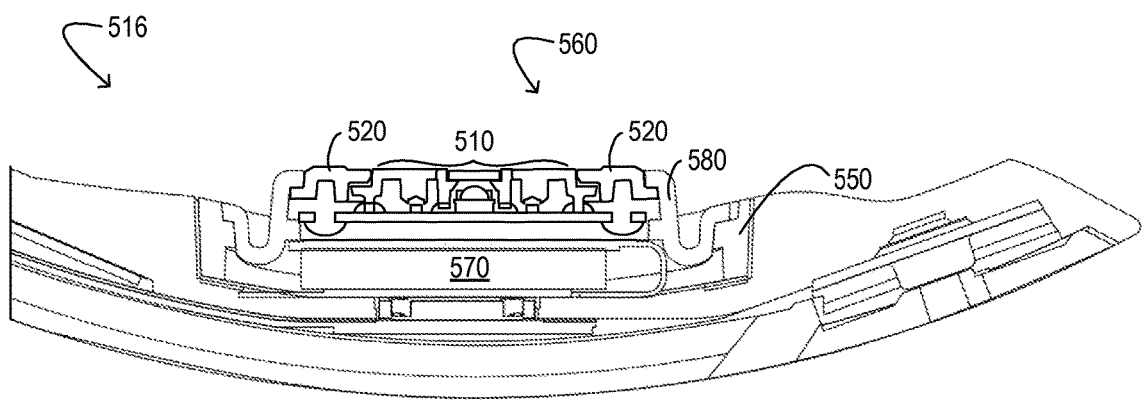
FIG. 5 is a cross-sectional view of a third example of a pillow assembly.

FIG. 5 is a cross-sectional view of a further example of a pillow assembly 516. Pillow assembly 516 may include substantially similar elements as pillow assembly 16W, including an optical pulse-rate sensor 560 (which include similar elements as optical pulse-rate sensor 60, including a window 510), frame 520 (which may be an electrically-conductive skin sensor such as a galvanic response sensor in one example), PCA, etc. Pillow assembly 516 includes a rolling diaphragm 580. Rolling diaphragm 580 may be comprised of a soft elastomer coupled to the frame 520 and a rigid housing 550 (or in some configurations, to a first region of a rigid or flexible pillow) to provide a gimbaling function so the optical pulse-rate sensor can skew on different planes and in several degrees of freedom. A spring element 570 biases the optical pulse-rate sensor against the skin of the wearer.

Compute system 22, via the sensory functions described herein, is configured to acquire various forms of information about the wearer of wearable electronic device 10. Such information must be acquired and used with utmost respect for the wearer's privacy. Accordingly, the sensory functions may be enacted subject to opt-in participation of the wearer. In implementations where personal data is collected on the device and transmitted to a remote system for processing, that data may be anonymized. In other examples, personal data may be confined to the wearable electronic device, and only non-personal, summary data transmitted to the remote system.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and nonobvious combinations and sub-combinations of the various processes, systems and configurations, and other features, functions, acts, and/or properties disclosed herein, as well as any and all equivalents thereof.

The invention claimed is:

1. A sensory-and-logic system, comprising:
an optical pulse-rate sensor comprising:
an illumination source configured to emit a blood-sensing light;
a first window portion of a window through which the blood-sensing light passes; and
an illumination receiver configured to measure the blood-sensing light reflected back through a second window portion of the window, wherein the first window portion, the second window portion, and all area between the first window portion and the second window portion are substantially level;
a wrist band assembly supporting the optical pulse-rate sensor and configured to encircle a wrist of a wearer;
a frame surrounding the window of the optical pulse-rate sensor and elevating away from the window toward a human tissue of the wrist of the wearer when the wrist band assembly encircles the wrist of the wearer, the frame having an inner frame portion level with the window and an outer frame portion elevated away from the inner frame portion toward the human tissue; and
a pillow surrounding the frame, the pillow including a first region surrounding the frame and level with the inner frame portion, and a second region sloping downward to the wrist band assembly.

2. The sensory-and-logic system of claim 1, wherein the window comprises a dichroic filter.

3. The sensory-and-logic system of claim 1, wherein the window comprises a light guide.

4. The sensory-and-logic system of claim 1, wherein the frame comprises a ring-shaped, electrically-conductive skin sensor sized and shaped to form an electrical connection with human skin.

5. The sensory-and-logic system of claim 1, wherein the pillow comprises a spring positioned under the illumination source, illumination receiver, window, and frame.

6. The sensory-and-logic system of claim 1, wherein the wrist band assembly further comprises a latching mechanism positioned under the optical pulse-rate sensor, frame, and pillow, and wherein the latching mechanism urges the pillow, frame, and optical pulse-rate sensor upward such that only the frame is in contact with the wrist of the wearer when the latching mechanism is latched.

7. A sensory-and-logic system, comprising:
an optical pulse-rate sensor comprising an illumination source configured to emit a blood-sensing light, a first window portion of a window through which the blood-sensing light passes, and an illumination receiver configured to measure the blood-sensing light reflected back through a second window portion of the window, wherein the first window portion, the second window portion, and all area between the first window portion and the second window portion are substantially level;
a wrist band assembly supporting the optical pulse-rate sensor and configured to encircle a wrist of a wearer;
a frame surrounding the window of the optical pulse-rate sensor, the frame having an inner frame portion level with the window and a rim elevated out from the inner frame portion toward the wrist and away from the wrist band assembly; and
a pillow surrounding the frame, the pillow including a first region surrounding the frame and a second region sloping to the wrist band assembly.

8. The sensory-and-logic system of claim 7, wherein the rim of the frame is elevated above the first region of the pillow.

9. A sensory-and-logic system, comprising:
an optical pulse-rate sensor comprising an illumination source configured to emit a blood-sensing light, a first window portion of a window through which the blood-sensing light passes, and an illumination receiver configured to measure the blood-sensing light reflected back through a second window portion of the window, wherein the first window portion, the second window portion, and all area between the first window portion and the second window portion are substantially level;
a wrist band assembly supporting the optical pulse-rate sensor and configured to encircle a wrist of a wearer;
a frame surrounding the window of the optical pulse-rate sensor, the frame having a rim positioned at a first vertical height relative to the wrist band assembly, the window positioned at a second vertical height relative to the wrist band assembly, the first vertical height greater than the second vertical height, and when the wrist band assembly is worn by the wearer, the rim is positioned closer to the wrist than the window; and
a pillow surrounding the frame, the pillow including a first region surrounding the frame, and a second region sloping to the wrist band assembly.

10. The sensory-and-logic system of claim 9, wherein the rim of the frame is elevated above the first region of the pillow.

* * * * *